(12) United States Patent
Hendriks et al.

(10) Patent No.: US 10,842,409 B2
(45) Date of Patent: Nov. 24, 2020

(54) POSITION DETERMINING APPARATUS AND ASSOCIATED METHOD

(71) Applicant: KONINKLIJKE PHILIPS N.V., Eindhoven (NL)

(72) Inventors: Bernardus Hendrikus Wilhelmus Hendriks, Eindhoven (NL); Harold Agnes Wilhelmus Schmeitz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 440 days.

(21) Appl. No.: 14/369,788

(22) PCT Filed: Dec. 24, 2012

(86) PCT No.: PCT/IB2012/057682
§ 371 (c)(1),
(2) Date: Jun. 30, 2014

(87) PCT Pub. No.: WO2013/102827
PCT Pub. Date: Jul. 11, 2013

(65) Prior Publication Data
US 2014/0357989 A1 Dec. 4, 2014

Related U.S. Application Data (60) Provisional application No. 61/582,514, filed on Jan. 3, 2012.

(51) Int. Cl.
*A61B 5/06* (2006.01)
*A61B 17/00* (2006.01)
(Continued)

(52) U.S. Cl.
CPC ........ *A61B 5/066* (2013.01); *A61B 17/00234* (2013.01); *A61B 34/20* (2016.02);
(Continued)

(58) Field of Classification Search
CPC ...... A61B 17/00234; A61B 2034/2051; A61B 2034/2055; A61B 2034/2061; A61B 2034/2065; A61B 34/20; A61B 5/066
(Continued)

(56) References Cited

U.S. PATENT DOCUMENTS 6,542,770 B2    4/2003   Zylka et al.
7,313,430 B2 * 12/2007   Urquhart ............... A61B 34/20
                                                            600/424
(Continued)

FOREIGN PATENT DOCUMENTS

JP      H105245 A     1/1998
JP    2007296341 A   11/2007
(Continued)

OTHER PUBLICATIONS

English translation of WO 2007/073988.*
(Continued)

*Primary Examiner* — Amanda Lauritzen Moher (57) ABSTRACT

The invention relates to a position determining apparatus (6) for determining the position of an interventional instrument (1) within a subject (4). A spatial relation between positions of a second part (3) of the interventional instrument outside the subject and a first part (2) of the interventional instrument within the subject is determined based on an actual image of the interventional instrument within the subject being preferentially an x-ray image and a provided position of the second part. Once the spatial relation has been determined, the position of the interventional instrument within the subject can be determined, while the interventional instrument is moved within the subject, based on the determined spatial relation and a determined actual position of the second part outside the subject, without necessarily acquiring a further actual image. This can allow for a (Continued)

reduction of a radiation dose, if rays are used for acquiring the actual image.

19 Claims, 2 Drawing Sheets

(51) Int. Cl.
  *A61B 34/20* (2016.01)
  *G06T 7/00* (2017.01)
(52) U.S. Cl.
  CPC .... *G06T 7/0012* (2013.01); *A61B 2034/2051* (2016.02); *A61B 2034/2055* (2016.02); *A61B 2034/2061* (2016.02); *A61B 2034/2065* (2016.02)
(58) Field of Classification Search
  USPC .......................................................... 600/424
  See application file for complete search history.

(56) References Cited

U.S. PATENT DOCUMENTS

| | | | |
|---|---|---|---|
| 8,208,993 B2 | 6/2012 | Piferi et al. | |
| 10,194,831 B2 | 2/2019 | Chan et al. | |
| 2004/0006268 A1* | 1/2004 | Gilboa | A61B 5/06 600/424 |
| 2004/0082849 A1* | 4/2004 | Schweikard | G06T 15/20 600/424 |
| 2004/0138555 A1* | 7/2004 | Krag | A61B 17/32053 600/424 |
| 2005/0049486 A1 | 3/2005 | Urquhart et al. | |
| 2006/0004286 A1* | 1/2006 | Chang | A61B 5/06 600/435 |
| 2008/0039716 A1* | 2/2008 | Tuma | A61B 90/36 600/424 |
| 2008/0071143 A1 | 3/2008 | Gattani et al. | |
| 2009/0124891 A1 | 5/2009 | Shechter et al. | |
| 2009/0149867 A1 | 6/2009 | Glozman et al. | |
| 2009/0281566 A1* | 11/2009 | Edwards | A61B 5/062 606/214 |
| 2010/0030063 A1 | 2/2010 | Lee et al. | |
| 2011/0268341 A1* | 11/2011 | Boese | A61B 6/4007 382/132 |
| 2012/0143203 A1 | 6/2012 | Nishio et al. | |
| 2012/0226481 A1 | 9/2012 | Carson | |
| 2013/0131499 A1* | 5/2013 | Chan | A61B 5/06 600/424 |

FOREIGN PATENT DOCUMENTS

| | | |
|---|---|---|
| WO | WO199956654 | 11/1999 |
| WO | 2007073988 A1 | 4/2007 |
| WO | WO2010067281 | 6/2010 |
| WO | WO2010145975 | 12/2010 |
| WO | WO2011141829 | 11/2011 |
| WO | WO2011024696 | 6/2012 |

OTHER PUBLICATIONS

N. Navab, et al., "Camera Augmented Mobile C-Arm (CAMC): Calibration, Accuracy Study, and Clinical Applications", IEEE Transactions on Medical Imaging, vol. 29, No. 7, Jul. 2010, pp. 1412-1423.
M. Mitschke, et al., "Interventions Under Video-Autmented X-Ray Guidance: Application to Needle Placement", MICCAI, 2000, pp. 858-868.
"Image-Guided Therapy Systems"; Advertisement for Philips Healthcare, Downloaded At https://www.philips.co.in/healthcare/solutions/interventional-xray, Koniklijke Philips N.V., 2004-2020. 5 page document.
"About NDI Medical"; Advertisement for Northern Digital Inc., Downloaded at https://www.ndigital.com/medical/polarisfaily.php, 2011, 2 page document.

* cited by examiner

POSITION DETERMINING APPARATUS AND ASSOCIATED METHOD

CROSS-REFERENCE TO PRIOR APPLICATIONS

This application is the U.S. National Phase application under 35 U.S.C. § 371 of International Application Serial No. PCT/IB2012/057682, filed on Dec. 24, 2012, which claims the benefit of U.S. Application Ser. No. 61/582,514, filed on Jan. 3, 2012. These applications are hereby incorporated by reference herein.

FIELD OF THE INVENTION

The invention relates to a position determining apparatus, a position determining method, and a position determining computer program for determining the position of an interventional instrument within a subject. The invention relates further to an interventional system, an interventional method and an interventional computer program for performing an interventional procedure.

BACKGROUND OF THE INVENTION

In interventional procedures generally an x-ray fluoroscopy system is used for generating x-ray fluoroscopy images, which show an interventional instrument within a patient. The position of the interventional instrument, in particular, the position of the tip of the interventional instrument, is then determined based on the x-ray fluoroscopy image and shown on a display for allowing a physician to perform the interventional procedure under guidance of the determined and shown position of the interventional instrument. The necessity to apply x-rays for determining the position of the interventional instrument within the patient leads to a relatively high radiation dose applied to the patient and to the personnel performing the interventional procedure.

SUMMARY OF THE INVENTION

It is an object of the present invention to provide a position determining apparatus, a position determining method and a position determining computer program for determining the position of an interventional instrument within a subject, wherein the radiation dose applied to the subject can be reduced. It is a further object of the present invention to provide an interventional system, an interventional method and an interventional computer program for performing an interventional procedure, which use the position apparatus.

In a first aspect of the present invention a position determining apparatus for determining the position of an interventional instrument within a subject is presented, wherein the interventional instrument comprises a first part to be introduced into the subject and a second part to be outside of the subject, when the first part is introduced into the subject, wherein the position determining apparatus comprises:

an image data set providing unit for providing an image data set of the interior of the subject, an instrument position providing unit for determining a position of the second part of the interventional instrument, an actual image providing unit for providing an actual image of the interventional instrument within the subject, a spatial relation determining unit for determining a spatial relation between the positions of the second part outside the subject and the first part within the subject based on the actual image and the position of the second part, and a position determining unit for determining the position of the first part within the provided image data set depending on the position of the second part and the spatial relation between the first part and the second part.

Since the spatial relation determining unit determines the spatial relation between the position of the second part outside the subject and the first part within the subject based on the actual image and the position of the second part, wherein the position determining unit determines the position of the first part within the provided image data set depending on the position of the second part and the spatial relation between the first part and the second part, the actual image, which will generally be generated by applying a radiation dose to the subject, is only needed for determining the spatial relation, but not for determining the position of the first part. Thus, once the spatial relation has been determined, the interventional instrument can be moved within the subject and the position of the interventional instrument within the subject can be determined based on the actual position of the second part outside the subject and the determined spatial relation, without necessarily requiring the generation of a further actual image. This allows reducing a radiation dose applied to the subject, if radiation is used for acquiring the actual image of the interventional instrument within the subject.

The interventional instrument is preferentially a needle or a catheter.

The image data set is preferentially a three-dimensional image data set like a computed tomography, magnetic resonance, ultrasound, single photon emission computed tomography, positron emission tomography et cetera data set. The image data set providing unit can comprise a storing unit, in which the image data set is stored already and from which the image data set can be provided. The image data set providing unit can also be a receiving unit for receiving the image data set via a wired or wireless data connection and for providing the received image data set. The image data set providing unit can also be the respective imaging modality itself.

The actual image providing unit is preferentially an x-ray imaging unit for acquiring an actual x-ray projection image of the interventional instrument within the subject. The actual image is preferentially a two-dimensional x-ray fluoroscopy image.

The position determining apparatus preferentially further comprises a display unit for displaying a representation of the first part at the determined position of the first part within the provided image data set.

In an interventional procedure it is generally important to know the position of the tip of the interventional instrument within the subject. The determined spatial relation provides therefore preferentially a spatial relation between one or several marks on the second part of the interventional instrument and the tip of the interventional instrument. The marks on the second part of the interventional instrument depend on the technique used by the instrument position providing unit for providing the position of the second part of the interventional instrument. For instance, the marks can be light sources like infrared light sources, wherein the instrument position providing unit can acquire at least two images of the light sources in different directions, detect the light sources in the at least two images and determine the position of the second part based on the positions of the detected light sources in the at least two images.

The subject is preferentially a living being like a patient or like an animal, wherein the position determining apparatus can be adapted to determine the position of the tip of, for instance, a needle or a catheter within the living being during a biopsy procedure, an ablation procedure, et cetera.

The provided image data set, the determined position of the second part and the actual image of at least the first part of the interventional instrument within the subject are preferentially related to or can be related to the same reference coordinate system, in order to allow the spatial relation determining unit to determine the spatial relation between the first and second parts and the position determining unit to determine the position of the first part within the provided image data set.

In an embodiment, the actual image is a two-dimensional image acquired by the actual image providing unit being a fluoroscopy imaging unit whose position can also be determined by the instrument position providing unit or by another position determining unit with respect to a three-dimensional reference coordinate system, wherein the spatial relation determining unit determines the two-dimensional position of the tip of the interventional instrument based on the two-dimensional image and converts the two-dimensional position to a three-dimensional position within the three-dimensional reference coordinate system. Moreover, preferentially the instrument position providing unit also determines the position of the second part with respect to the three-dimensional reference coordinate system, wherein the spatial relation determining unit determines the spatial relation between the first part and the second part depending on the determined positions of the first and second parts.

It is preferred that the spatial relation determining unit is adapted to determine the position of the distal tip of the interventional instrument based on the actual image and to determine a spatial relation between the position of the second part outside the subject, in particular, of markers on the second part, and the position of the first part by determining a spatial relation between the position of the second part outside the subject and the determined position of the distal tip within the subject, wherein the position determining unit is adapted to determine the position of the distal tip within the provided image data set depending on the position of the second part and the spatial relation between the distal tip and the second part. In particular, the actual image providing unit can be adapted to provide an actual image of the interventional instrument within the subject, which shows the distal tip of the first part of the interventional instrument, wherein the spatial relation determining unit is adapted to determine the position of the distal tip within the subject by detecting the distal tip in the actual image. This allows accurately determining the position of the distal tip of the interventional instrument within the subject.

The spatial relation determining unit can provide a graphical user interface for allowing a user to indicate the position of the distal tip in the actual image for detecting the position of the distal tip, and/or the spatial relation determining unit can be adapted to use known segmentation techniques, for example, based on thresholding, for detecting the position of the distal tip in the actual image.

The first part of the interventional instrument is preferentially longish and bendable. In an embodiment, it has a known length within the subject, wherein the spatial relation determining unit is adapted to detect the shape, in particular, a bending, of the interventional instrument within the subject and to determine the position of the distal tip within the subject depending on the detected shape within the subject and the known length within the subject. Moreover, the actual image may show only an intermediate region of the first part of the interventional instrument within the subject, wherein the spatial relation determining unit can be adapted to detect the shape of the intermediate region, thereby detecting a pathway of the intermediate region within the subject, and to determine the position of the distal tip by extrapolating the detected pathway to the end of the known length within the subject. This allows determining the position of the distal tip within the subject accurately, even if the distal tip itself is not visible in the actual image.

In an embodiment, the spatial relation determining unit is adapted to perform an optical shape sensing procedure for determining a spatial relation between the position of the second part outside the subject and the first part within the subject, wherein the spatial relation is determined based on the shape of the first part within the subject and the position of the second part outside the subject, wherein the shape of the first part within the subject is determined by optical shape sensing with the constraint that the determined shape of the first part has to correspond to the shape of the first part shown in the actual image. The actual image can therefore be used for improving the accuracy of an optical shape sensing procedure. The optical shape sensing procedure can be performed in accordance with the procedure disclosed in WO 2011/141829 A1, which is herewith incorporated by reference.

Preferentially, the actual image providing unit is adapted to provide at least two actual images, which have been acquired in different acquisition directions, wherein the spatial relation determining unit is adapted to determine the position of the first part within the subject based on the provided at least two actual images. This further increases the accuracy of determining the spatial relation and, thus, of determining the position of the first part within the subject.

In a preferred embodiment, the spatial relation determining unit is adapted to determine the spatial relation by correcting an initially provided spatial relation based on the first part within the subject shown in the actual image and the position of the second part. The use of an accurately determined initial spatial relation for determining an actual spatial relation can further increase the accuracy of determining the spatial relation and, thus, of determining the position of the first part within the subject.

The determined spatial relation provides preferentially a spatial relation between one or several marks on the second part of the interventional instrument and one or several locations on the first part. For instance, the spatial relation can be a spatial relation between one or several marks on the second part of the interventional instrument and the distal tip of the interventional instrument. For determining the spatial relation the position of the tip and/or the shape of the interventional instrument within the subject can be detected in the actual image, wherein this position and/or shape information can be used for determining the spatial relation between the second part outside the subject and the first part within the subject. In an embodiment, the spatial relation is initially provided by positioning the tip of the interventional instrument at a known reference location and by determining the position of the one or several marks on the second part.

It is further preferred that the instrument position providing unit is adapted to determine the position of the second part of the interventional instrument by at least one of an optical or magnetic technique. For instance, for determining the position of the second part of the interventional instrument, in particular, for tracking the second part of the interventional instrument, while the interventional instrument is moved, the instrument position providing unit can be adapted to use the optical tracking methods disclosed in WO 1999/056654 A1, which is herewith incorporated by reference. In particular, the second part of the interventional instrument can comprise infrared light sources as markers located at positions, in particular which are known with respect to the interventional instrument, wherein the instrument position providing unit can comprise at least two cameras for generating images showing the infrared light sources and determine the position of the second part of the interventional instrument depending on the positions of the infrared light sources in the generated images.

In a further aspect of the present invention an interventional system for performing an interventional procedure is presented, wherein the interventional system comprises:

an interventional instrument for performing an interventional procedure within a subject, and a position determining apparatus for determining the position of the interventional instrument within the subject as defined in claim 1.

In a further aspect of the present invention a position determining method for determining the position of an interventional instrument within a subject is presented, wherein the interventional instrument comprises a first part to be introduced into the subject and a second part to be outside of the subject, when the first part is introduced into the subject, wherein the position determining method comprises:

providing an image data set of the interior of the subject by an image data set providing unit, determining a position of the second part of the interventional instrument by an instrument position providing unit, providing an actual image of the interventional instrument within the subject by an actual image providing unit, determining a spatial relation between the positions of the second part outside the subject and the first part within the subject based on the actual image and the position of the second part by a spatial relation determining unit, and determining the position of the first part within the provided image data set depending on the position of the second part and the spatial relation between the first part and the second part by a position determining unit.

In a further aspect of the present invention an interventional method for performing an interventional procedure is presented, wherein the interventional method comprises:

performing an interventional procedure within a subject by an interventional instrument, and determining the position of the interventional instrument within the subject as defined in claim 12 by a position determining apparatus.

In a further aspect of the present invention a position determining computer program for determining a position of an interventional instrument within a subject is presented, wherein the position determining computer program comprises program code means for causing a position determining apparatus as defined in claim 1 to carry out the steps of the position determining method as defined in claim 12, when the computer program is run on a computer controlling the position determining apparatus.

In a further aspect of the present invention an interventional computer program for performing an interventional procedure is presented, wherein the interventional computer program comprises program code means for causing an interventional system as defined in claim 11 to carry out the steps of the interventional method as defined in claim 13, when the computer program is run on a computer controlling the interventional system.

It shall be understood that the position determining apparatus of claim 1, the interventional system of claim 11, the position determining method of claim 12, the interventional method of claim 13, the position determining computer program of claim 14, and the interventional computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
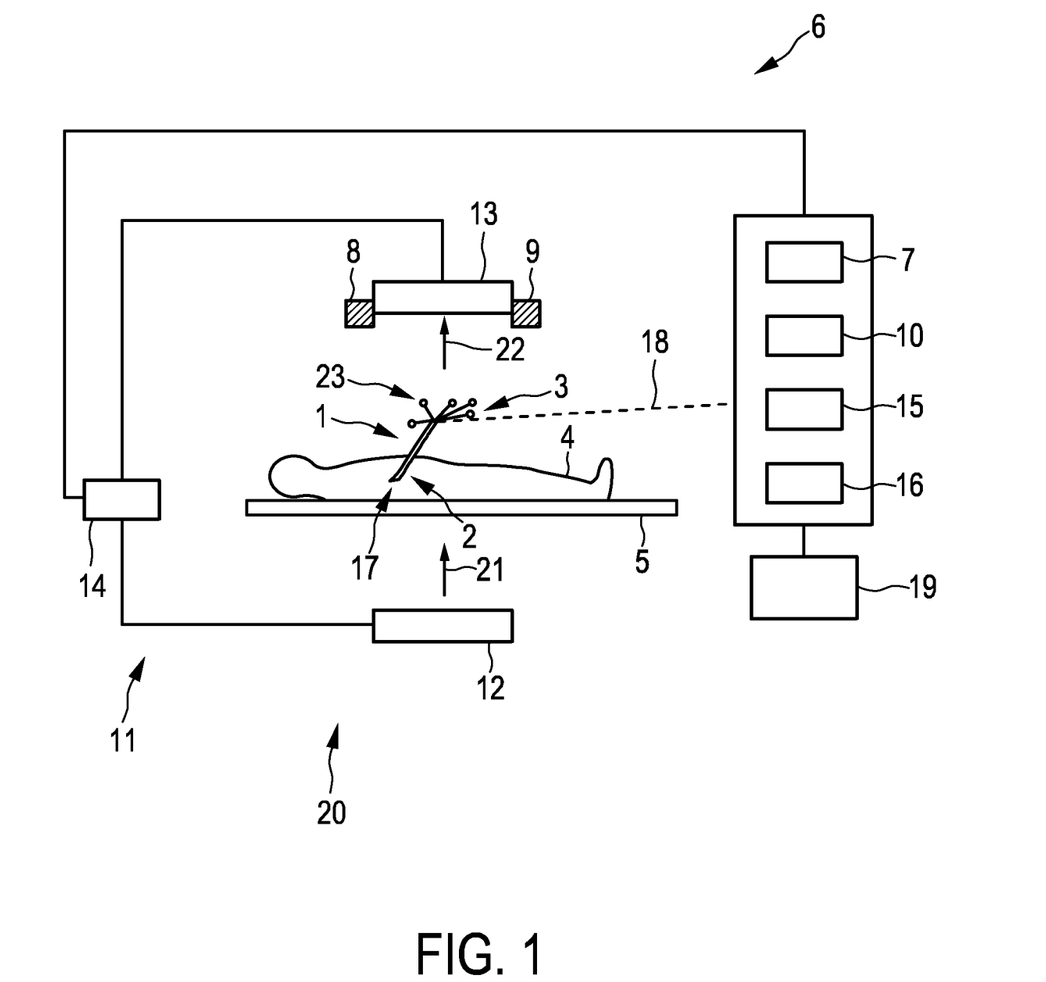
FIG. 1 shows schematically and exemplarily an embodiment of an interventional system for performing an interventional procedure.

FIG. 1 shows schematically and exemplarily an embodiment of an interventional system 20 for performing an interventional procedure. The interventional system 20 comprises an interventional instrument 1 being, in this embodiment, a needle for performing an interventional procedure within a patient 4 being located on a table 5. The interventional system 20 further comprises a position determining apparatus 6 for determining the position of the interventional instrument 1 within the patient 4. The interventional instrument 1 comprises a first part 2 to be introduced into the patient 4 and a second part 3 to be outside of the patient 4, when the first part 2 is introduced into the patient 4.

The position determining apparatus 6 comprises an image data set providing unit 7 for providing an image data set of the interior of the patient 4, an instrument position providing unit 8, 9, 10 for determining a position of the second part 3 of the interventional instrument 1, and an actual image providing unit 11 for providing an actual image of the interventional instrument 1 within the patient 4. The position determining apparatus 6 further comprises a spatial relation determining unit 15 for determining a spatial relation between the position of the second part 3 outside the patient 4 and the first part 2 within the patient 4 based on the actual image and the position of the second part 3, and a position determining unit 16 for determining the position of the first part 2 within the provided image data set depending on the position of the second part 3 and the spatial relation between the first part 2 and the second part 3.

The actual image providing unit 11 is an x-ray imaging unit for acquiring an actual x-ray projection image of the interventional instrument 1 within the patient 4 during the interventional procedure. In this embodiment, the actual image providing unit 11 is a C-arm x-ray fluoroscopy system acquiring a two-dimensional x-ray fluoroscopy image for providing the actual image of the interventional instrument 1 within the patient 4. It comprises an x-ray source 12 for generating x-rays 21 to be directed to a region within the patient 4, where the interventional instrument 1 is located. The generated x-rays 21 traverse the patient 4 and the traversed x-rays 22 are detected by an x-ray detection unit 13. The x-ray source 12 and the x-ray detection unit 13 are mounted on a C-arm such that they can be moved, in particular, rotated, with respect to the patient 4, in order to allow the actual image providing unit 11 to provide an actual image showing a desired region within the patient 4 in a desired direction. The x-ray source 12 and the x-ray detection unit 13 are controlled by a fluoroscopy control unit 14.

The image data set is a three-dimensional image data set being, in this embodiment, a three-dimensional computed tomography image data set. In other embodiments, the image data set can also be a two-dimensional image data set. Moreover, the image data set can be the image data set of another imaging modality like a magnetic resonance, ultrasound, single photon emission computed tomography, positron emission tomography, et cetera image data set. The image data set providing unit 7 is a storing unit, in which the image data set is stored already and from which the image data set can be provided. The image data set providing unit can also be a receiving unit for receiving the image data set via a wired or wireless data connection and for providing the received image data set. Moreover, in another embodiment, the image data set providing unit can also be the respective imaging modality itself. In this embodiment, the actual image providing unit 11 is adapted to acquire projection images of the patient 4 in different directions and to reconstruct a computed tomography image as the provided image data set, which is stored in the storing unit, based on the projection data before performing the interventional procedure. However, the image data set can also be generated by a computed tomography system.

The instrument position providing unit is adapted to determine the position of the second part 3 of the interventional instrument 1 optically. The instrument position providing unit comprises two cameras 8, 9 for acquiring images of markers 23 attached to the second part 3 of the interventional instrument 1. The markers 23 can be passive markers, which do not actively send optical radiation to the cameras 8, 9, or they can be active markers, i.e. light sources sending radiation to the cameras 8, 9. For instance, the markers 23 can be infrared light sources and the cameras 8, 9 can be infrared cameras for acquiring infrared images showing the infrared light sources 23. The images acquired by the cameras 8, 9 are provided to an instrument position determining unit 10 for determining the position of the second part 3 of the interventional instrument 1, in particular, of the marker 23 on the second part 3, based on the positions of the markers 23 in the acquired images. If desired, the position of the entire second part 3 can then be determined based on the known real positions of the markers 23 with respect to the second part 3 of the interventional instrument 1 and the determined positions of the markers 23. For determining the position of the second part 3 based on the images acquired by the cameras 8, 9 known tracking algorithms can be used like the tracking algorithm disclosed in WO 1999/056654 A1, which is herewith incorporated by reference. Also other known optical or non-optical, for instance, magnetic, tracking techniques can be used for determining the position of the second part 3 of the interventional instrument 1 outside of the patient 4.

In this embodiment, the spatial relation determining unit 15 is adapted to determine the position of the distal tip 17 of the interventional instrument 1 based on the actual image and to determine a spatial relation between the position of the second part 3 outside the patient 4 and the position of the first part 2 by determining a spatial relation between the position of the second part 3, in particular, of the markers 23 of the second part, outside the patient 4 and the determined position of the distal tip 17 within the patient 4, wherein the position determining unit 16 is adapted to determine the position of the distal tip 17 within the provided image data set depending on the position of the second part 3 and the spatial relation between the distal tip 17 and the second part 3. In particular, the actual image providing unit 11 is adapted to provide an actual image of the interventional instrument 1 within the patient 4, which shows the distal tip 17 of the first part 2 of the interventional instrument 1, wherein the spatial relation determining unit 15 is adapted to determine the position of the distal tip 17 within the subject 4 by detecting the distal tip 17 in the actual image. The spatial relation determining unit 15 can provide a graphical user interface for allowing a user to indicate the position of the distal tip 17 in the actual image for detecting the position of the distal tip 17 and/or the spatial relation determining unit 15 can be adapted to use known segmentation techniques, for example, based on thresholding, for detecting the position of the distal tip 17 in the actual image.

The determination of the spatial relation can be performed by correcting an initially provided spatial relation based on the first part 2 within the patient 4 shown in the actual image and the position of the second part 3. For determining the initial spatial relation the distal tip 17 of the interventional instrument 1 can be located at a known location outside of the patient 4 before the interventional procedure is performed, while the position of the second part 3, in particular, of the markers 23, is determined by the instrument position providing unit 8, 9, 10. Thus, the initial spatial relation can be provided by a calibration procedure, wherein the tip 17 is placed at a known reference point.

In particular, based on the determined position of the second part 3 of the interventional instrument 1 and the initially provided spatial relation an uncorrected position of the distal tip 17 within the patient 4 can be determined during the interventional procedure. A projection plane can be defined, which contains this uncorrected position and which is perpendicular to the axis of the fluoroscopy system 11 connecting the x-ray source 12 and the x-ray detector 13. On this projection plane the real position of the distal tip 17 in the actual image, i.e. in the fluoroscopy image, can be virtually projected, whereupon an offset between the uncorrected distal tip position and the real distal tip position can be determined. This offset can be added to the initial spatial relation between the distal tip and the second part, in particular, between the distal tip and the markers on the second part, for correcting the spatial relation, thereby determining the actual spatial relation between the position of the second part 3 outside the patient 4 and the position of the first part 2 within the subject 4.

The cameras 8, 9 are rigidly attached to the x-ray detector 13 such that the instrument position providing unit 8, 9, 10 and the actual image providing unit 11 are registered with respect to each other, i.e. the relevant positions of the first and second parts, in particular, of the markers on the second part and of the distal tip, are known with respect to a same reference coordinate system, in which the detection and determination procedures can be performed. Alternatively or in addition, cameras can be rigidly attached to a C-arm holding the x-ray source 12 and the x-ray detector 13. If in another embodiment the instrument position providing unit and the actual image providing unit are not rigidly attached to each other, they can be registered by other means. For instance, the instrument position providing unit can also be adapted to determine the position of the actual image providing unit, in particular, of the fluoroscopy system 11, in order to register the actual image providing unit and the instrument position providing unit with respect to each other. For determining the position of the actual image providing unit the actual image providing unit can comprise markers, which can be detected by the instrument position providing unit.

The provided image data set is registered with respect to the positions and images provided by the instrument position providing unit and the actual image providing unit. This registration can automatically be achieved, if, for instance, the actual image providing unit 11 is not only used for providing one or several actual images, but also used for providing projection data, which are used for reconstructing the image data set, i.e., in this embodiment, the x-ray computed tomography image data set. Alternatively or in addition, other registration techniques can be used for registering the image data set of the interior of the patient 4 with the positions and images provided by the instrument position providing unit and the actual image providing unit. For instance, features being visible in the actual image and the image data set, can be used for registering the actual image and the image data set with respect to each other.

The position determining apparatus 6 further comprises a display unit 19 for displaying a representation of the first part 2, in particular, of the distal tip 17, at the determined position within the provided image data set, i.e., in this embodiment, within the three-dimensional computed tomography image data set.

The fluoroscopy system 11 can provide two or more actual images, i.e. two or more two-dimensional x-ray fluoroscopy images, which have been acquired in different acquisition directions, wherein the spatial relation determining unit 15 can be adapted to determine the position of the first part 2, in particular, the position of the distal tip 17, within the patient 4 based on the provided at least two actual images.

The first part 2 of the interventional instrument 1 is preferentially a longish, bendable part. In an embodiment, the length of the part of the interventional instrument 1 within the patient 4 is known and the actual image does not show the distal tip 17 of the interventional instrument. The length of the interventional instrument 1 within the patient 4 can be known, for instance, from markers, which are just outside the patient 4 and to which the respective length within the patient 4 has been assigned, or the length of the interventional instrument outside of the patient 4 can be determined and subtracted from the overall length of the interventional instrument 1. In this embodiment, the spatial relation determining unit 15 can be adapted to detect the shape, in particular, the bending, of the interventional instrument 1 within the patient 4 and to determine the position of the distal tip 17 within the patient 4 depending on the detected shape within the patient 4 and the known length within the patient 4. The actual image may only show an intermediate region of the first part 2 of the interventional instrument 1 within the patient 4, wherein the spatial relation determining unit 15 may be adapted to detect the shape of the intermediate region, thereby detecting a pathway of the intermediate region within the patient 4, and to determine the position of the distal tip 17 by extrapolating the detected pathway to the end of the known length within the patient 4.

In a further embodiment, the spatial relation determining unit can be adapted to perform an optical shape sensing procedure for determining a spatial relation between the position of the second part 3 outside the patient 4 and the first part 2 within the patient 4, wherein the spatial relation is determined based on the shape of the first part 2 within the patient 4 and the position of the second part 3 outside the patient 4 and wherein the shape of the first part 2 within the patient 4 is determined by optical shape sensing with the constraint that the determined shape of the first part 2 has to correspond to the shape of the first part 2 shown in the actual image. In particular, the shape of the first part 2 determined by optical shape sensing can be virtually projected onto the two-dimensional detection surface of the x-ray detection unit 13, wherein the optical shape sensing procedure can determine the shape of the first part 2 within the patient 4 such that the projected shape is similar to the shape of the first part detected in the actual image. For performing the optical shape sensing procedure the interventional instrument can comprise optical fibers and the interventional instrument is connected via an optional optical connection 18 with the spatial relation determining unit for allowing the spatial relation determining unit to determine the shape of the first part of the interventional instrument within the patient. The known optical shape sensing technique is based on an iterative reconstruction of the three-dimensional fiber shape based on measurements on strain in the optical fibers. For a more detailed description of this known optical shape sensing procedure reference is made to, for instance, WO 2011/141829 A1, which is herewith incorporated by reference.

Figure 2:
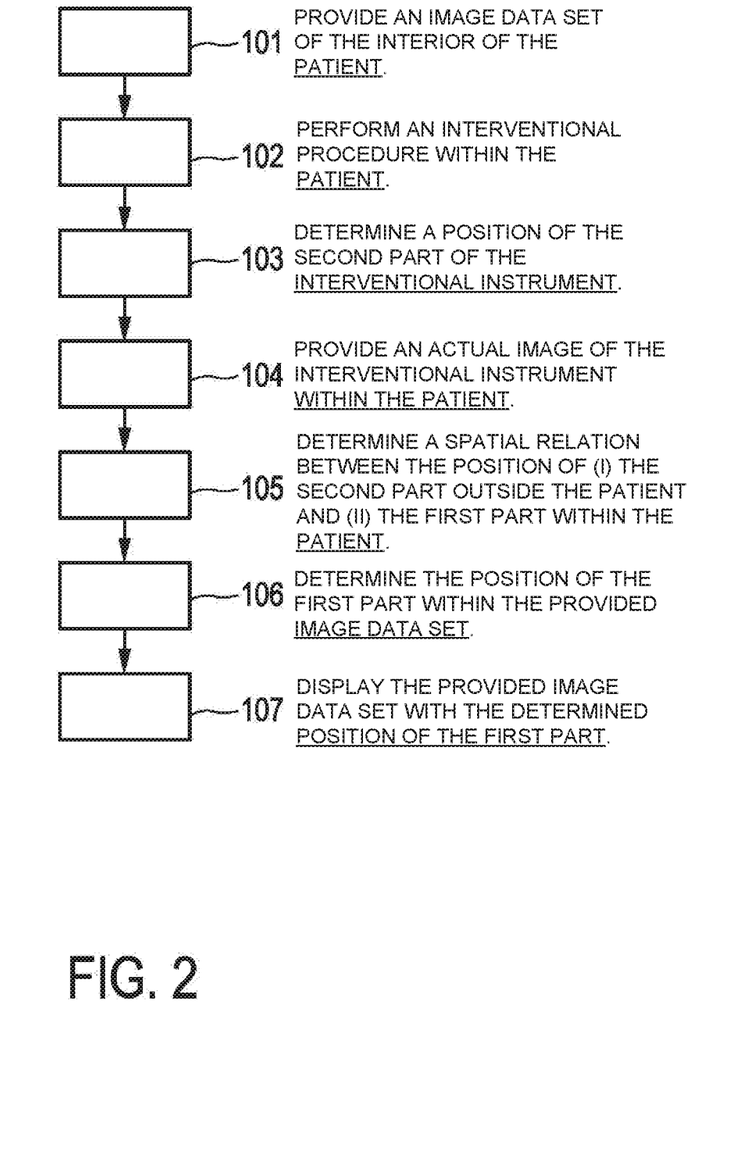
FIG. 2 shows a flowchart exemplarily illustrating an embodiment of an interventional method for performing an interventional procedure.

In the following an embodiment of an interventional method for performing an interventional procedure will exemplarily be described with reference to a flowchart shown in FIG. 2.

In step 101, an image data set of the interior of a patient is provided by the image data set providing unit 7. In particular, a three-dimensional computed tomography image of the patient 4 is provided. In step 102, an interventional procedure within the patient 4 is performed by using the interventional instrument 1. For instance, a needle is introduced into the patient 4. Then, in step 103, a position of the second part of the interventional instrument is determined by the instrument position providing unit 8, 9, 10, and in step 104 an actual image of the interventional instrument within the patient 4 is provided by the actual image providing unit 11. In step 105, a spatial relation between the position of the second part outside the patient and the first part within the patient is determined based on the actual image and the position of the second part by the spatial relation determining unit 15. In step 106, the position of the first part within the provided image data set is determined depending on the position of the second part and the spatial relation between the first part and the second part by the position determining unit 16, wherein in step 107 the display unit 19 displays the provided image data set with the determined position of the first part.

In other embodiments, these steps can be performed in another order. For instance, the position of the second part of the interventional instrument can be determined after the provision of the actual image, or these determination and provision operations can be performed simultaneously. Moreover, also steps 105 and 106 can be performed simultaneously. For instance, the spatial relation can be determined by correcting an uncorrected determined position of the first part within the patient, which has been determined based on an initially provided spatial relation, wherein based on the actual position of the first part shown in the actual image, the determined position of the first part can be corrected, thereby simultaneously correcting and, thus, determining the spatial relation and the position of first part within the patient. If the interventional procedure continues, for instance, if the interventional instrument is further moved within the patient, the actual position of the first part, in particular of the distal tip of the interventional instrument, can be determined based on the corrected spatial relation and the actual position of the second part, without necessarily requiring a further actual image, in particular, without requiring a further x-ray fluoroscopy image.

Steps 102 to 107 can be regarded as being the steps of a position determining method for determining the position of an interventional instrument within a subject.

Interventional device tracking, i.e. interventional instrument tracking, during minimally invasive procedures in a human body is important, in order to be able to reach accurately a correct location for diagnosis or treatment. A way to track the interventional device is by using x-ray guidance. Although tracking can be performed with x-ray guidance, a drawback is the x-ray dose that is applied to both, the patient and the physician. In order to reduce this x-ray dose, optical guidance has been introduced based on several cameras attached to the detector of the x-ray device as disclosed in, for instance, WO 1999/056654 A1. This optical guidance allows instrument tracking without x-ray dose based on three-dimensional imaging of the interventional device outside of the patient and on the three-dimensional imaging of the patient. A drawback of this optical technique is that the inside of the body can not be seen and the tracking of the device is therefore based on what can be seen outside of the body. A problem that arises with this known optical guidance method is the moment the interventional device is deforming, for instance, the bending of a needle during insertion, the optical guidance method becomes less accurate.

The position determining apparatus described above with reference to FIG. 1 can improve the localization of the distal tip of the interventional device when tracked optically, while minimizing the required x-ray dose. The position determining apparatus can solve the prior art problem of an inaccurate localization of the tip of the interventional instrument by performing the interventional instrument tracking with the optical markers described in WO 1999/056654 A1, wherein during the insertion of the interventional instrument at least one actual image, i.e. at least one two-dimensional x-ray fluoroscopy image, is taken, wherein from this image the bending of the interventional instrument or the actual position of the tip of the interventional instrument is inferred and wherein the bending or the actual position of the tip is used in the optical tracking to correct the prediction of the tip of the interventional instrument inside the body. In case during the further insertion of the interventional instrument bending deviating from the previous detected bending or a bending leading to a tip position being different to the predicted tip position is expected, a physician can perform an additional update of determining the deformation of the interventional instrument or of determining the actual tip position, in order to obtain a more accurate optical guidance. Thus, based on the actual image a spatial relation between the outer part of the interventional instrument being outside of the patient, in particular, between markers on this outside part of the interventional instrument, and the tip within the patient can be corrected, wherein the optical guidance can then be based on this corrected spatial relation, thereby improving the accuracy of the optical guidance. For determining the deformation of the interventional instrument and/or the position of the tip within the patient, preferentially two fluoroscopy images are taken with different angles.

The interventional system can be adapted to co-register the instrument position providing unit being preferentially an optical guidance system, the actual image providing unit being preferentially a fluoroscopy system, and the image data set being, for instance, a three-dimensional image data set from a computed tomography system, a magnetic resonance imaging system or a combined positron emission tomography and computed tomography imaging system. A trajectory, along which the interventional instrument should be inserted into the patient, and/or a location of interest, to which the interventional instrument should be navigated, can be determined in the provided image data set. In particular, a user can indicate the trajectory and/or the location of interest in the image data set, which may be shown on the display unit 19, by using, for instance, a graphical user interface and input means like a keyboard or a mouse. The interventional system can also comprise a trajectory and/or location of interest determining unit for automatically determining the trajectory and/or the location of interest. The user can then guide the interventional instrument along the determined trajectory and/or towards the location of interest by using the instrument position providing unit being preferentially an optical guidance system, wherein the determination of the position of the interventional instrument within the patient is based on the visible second part of the interventional instrument outside the body. Then, an actual image being preferentially a fluoroscopy image of the partially inserted interventional instrument can be acquired and can be used to determine the bending of the first part within the body and/or the position of the distal tip within the body. The bending information and/or the information about the actual position of the distal tip of the interventional instrument can then be used for correcting the optical guidance of the interventional instrument. The further guidance of the interventional instrument towards a desired location within the body can then be performed based on the corrected optical guidance, which uses a corrected spatial relation between the visible outer second part of the interventional instrument and the inner first part of the interventional instrument.

The interventional instrument can be registered with the instrument position providing unit being preferentially an optical tracking system by placing the tip of the interventional instrument against a known reference point and by measuring the location of markers on the second part of the interventional instrument relative to the reference point. Due to deflection or bending of the interventional instrument during use the tip location may differ from the calibrated position such that in known interventional systems the tracking may be inaccurate. However, by using the interventional system described above with reference to FIG. 1 the position of the tip within the patient can accurately be determined, even if the interventional instrument is deflected or bent.

In particular, after the interventional instrument has been calibrated by a physician by placing the tip of the interventional instrument at a known reference point, a target location within the patient can be determined. The interventional instrument can then partially be inserted into the patient, wherein the position of the tip of the interventional instrument can be determined based on a determined position of the outer second part of the interventional instrument and an initial spatial relation between the second part outside the patient, in particular, the markers of the second part outside the patient, and the tip of the interventional instrument as determined by the calibration of the position determining apparatus. Then, an actual image, i.e. preferentially a fluoroscopy image, can be acquired, wherein the fluoroscopy image shows the tip of the interventional instrument. The two-dimensional location of the tip of the interventional instrument in the actual image can be determined either manually or automatically by means of computer vision algorithms, and can be converted to a three-dimensional reference coordinate system by combining the pose of the actual image providing unit, in particular, of the fluoroscopy system, and the tracked interventional instrument. Both poses can be provided by the instrument position providing unit, in particular, by the optical tracking system, and/or by position encoders. Then, the calibration of the interventional instrument, i.e. the spatial relation defining the location of the tip of the interventional instrument relative to the markers of the second part of the interventional instrument, can be updated by adjusting the tip location perpendicular to the axis of the actual image providing unit, i.e. by adjusting the tip location within or parallel to the image plane. If desired, at least one additional actual image from a different angular direction, in particular, from an angular direction being perpendicular to the angular direction of the first actual image, can be used for providing a full three-dimensional correction of the tip location. The physician can then continue the interventional procedure under guidance of the position determining apparatus, in particular, under optical guidance, by using the updated instrument calibration, i.e. by using the updated spatial relation between the markers on the second part of the interventional instrument and the tip of the interventional instrument. Thus, while the physician navigates the interventional instrument within the patient, the display unit can show the determined position of the tip of the interventional instrument within the patient in the provided three-dimensional image data set being preferentially a three-dimensional computed tomography image data set, wherein the determination of the position of the tip within the patient is based on the corrected spatial relation. The acquisition of the actual image, the correction of the spatial relation based on the actual image and, thus, the correction of the determined tip position within the patient can be repeated as desired.

Instead of performing an initial calibration procedure for determining an initial spatial relation between the second part, in particular, markers of the second part, and the tip of the interventional instrument, the position determining method and the interventional method may be performed without such an initial calibration. For instance, if the interventional instrument is a longish instrument like a needle, the position determining unit can determine firstly an approximate tip location being defined by a line, which is determined as an extension of the second part of the interventional instrument outside of the patient in the direction determined by the instrument position providing unit. The interventional instrument may partly be inserted into the patient, while the display unit may show the approximate tip location, i.e. a corresponding line, within the provided image data set showing the interior of the patient. The physician can mark the target depths on the interventional instrument and stop insertion well before the target would be reached.

If the length of the interventional instrument within the patient is unknown, without using the actual image of the interventional instrument within the patient the position determining unit can only determine the approximate tip location defined by the extension line, but not the exact position of the tip of the interventional instrument. However, the spatial relation determining unit can determine the spatial relation between the tip of the interventional instrument and markers on the second part of the interventional instrument based on the determined position of the second part of the interventional instrument, in particular, of the markers on the second part, and the actual image showing the tip of the interventional instrument. The further guidance of the physician can then be based on the determined spatial relation, i.e. the position determining unit can determine the position of the tip within the provided image data set depending on the position of the second part of the interventional instrument and the spatial relation between the tip of the interventional instrument and the second part, wherein the determined position of the tip within the image data set can be shown on the display unit, in order to allow the physician to navigate the interventional instrument based on the actual position of the tip within the patient as shown on the display unit.

As an add-on to the position determining apparatus an extrapolation of instrument deformation can be performed. Some interventional instruments like a needle with an asymmetric tip tend to drift to one direction. From at least one actual image the needle's curvature can be extracted and used to predict the amount and direction of the drift. As the needle is inserted, the predicted tip location can be updated as a function of the drift and the inserted length. By updating the predicted tip location the spatial relation between the tip of the interventional instrument and the second part of the interventional instrument is updated, wherein the updated spatial relation can be used for determining the position of the tip of the interventional instrument, while the interventional instrument is further navigated to a desired location.

The interventional system can comprise a warning unit for providing a warning, if the determined position of the first part of the interventional instrument deviates from a planned trajectory.

Although in the above described embodiments the instrument position providing unit comprises an optical tracking system using two cameras, in other embodiments the instrument position providing unit can also comprise another optical or non-optical tracking system like the mentioned optical shape sensing system, electro-magnetic tracking systems, articulated arms, radio frequency tracking systems et cetera.

The interventional system and the position determining apparatus can be used during minimally invasive procedures requiring device tracking by x-ray such as needle biopsies, radio frequency ablations, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the spatial relation and the determination of the position of the first part within the subject performed by one or several units or devices can be performed by any other number of units or devices. For instance, steps 105 and 106 can be performed by a single unit or by any other number of different units. The determinations and/or the control of the interventional system in accordance with the interventional method and/or the control of the position determining apparatus in accordance with the position determining method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a position determining apparatus for determining the position of an interventional instrument within a subject. A spatial relation between positions of a second part of the interventional instrument outside the subject and a first part of the interventional instrument within the subject is determined based on an actual image of the interventional instrument within the subject being preferentially an x-ray image and a provided position of the second part. Once the spatial relation has been determined, the position of the interventional instrument within the subject can be determined, while the interventional instrument is moved within the subject, based on the determined spatial relation and a determined actual position of the second part outside the subject, without necessarily acquiring a further actual image. This can allow for a reduction of a radiation dose, if x-rays are used for acquiring the actual image.

The invention claimed is:

1. A system for determining positions of an interventional instrument within a subject, the system comprising:
 a computer, wherein the computer is configured to run a computer program to:
 provide an image data set of an interior of the subject as a provided image data set;
 subsequent to a first part of the interventional instrument being introduced into the subject, determine positions of a second part of the interventional instrument outside of the subject;
 acquire an x-ray projection image, separate from the provided image data set, of the first part of the interventional instrument introduced within the subject;
 determine a spatial relation between the positions of the second part and positions of the first part based on (i) the x-ray projection image of the first part introduced within the subject and (ii) the positions of the second part; and
 determine positions of the first part within the provided image data set, without having to further image the first part, based on images that are only from the provided image data set and the x-ray projection image, and based on the positions of the second part and the spatial relation between the positions of the second part and the positions of the first part, as determined via determining the spatial relation between the positions of the second part and the positions of the first part.

2. The system of claim 1, wherein the computer program is further run to:
 determine a position of a distal tip of the first part based on the x-ray projection image and determine the spatial relation between the positions of the second part and the positions of the first part by determining a spatial relation between the positions of the second part and the position of the distal tip, and
 determine the position of the distal tip within the provided image data set depending on (i) the positions of the second part and (ii) the spatial relation between the positions of the second part and the position of the distal tip.

3. The system of claim 2,
 wherein the x-ray projection image shows the distal tip of the first part within the subject; and
 wherein the computer program is further run to determine the position of the distal tip within the subject by detecting the distal tip in the x-ray projection image.

4. The system of claim 2, wherein the first part is a bendable part having a known length within the subject, and
 wherein the computer program is further run to:
 detect a shape of the first part within the subject as a detected shape, and determine the position of the distal tip within the subject depending on the detected shape and the known length within the subject.

5. The system of claim 4, wherein the x-ray projection image shows an intermediate region of the first part within the subject, and
 wherein the computer program is further run to:
 detect a shape of the first part, thereby detecting a pathway of the intermediate region within the subject as a detected pathway, and determine the position of the distal tip by extrapolating the detected pathway to an end of the known length within the subject.

6. The system of claim 1, wherein the spatial relation between the positions of the second part and the positions of the first part is determined further based on (i) a shape of the first part within the subject and (ii) the positions of the second part, wherein the shape of the first part within the subject is determined by optical shape sensing with a constraint that the shape of the first part has to correspond to an actual shape of the first part shown in the x-ray projection image.

7. The system of claim 1, wherein the computer program is further run to:
 provide at least two x-ray projection images including the x-ray projection image, wherein the at least two x-ray projection images have been acquired in different acquisition directions, and
 determine the positions of the first part based on the at least two x-ray projection images.

8. The system of claim 1, wherein the spatial relation between the positions of the second part and the positions of the first part is further determined by correcting another spatial relation that is initially provided based on (i) the first part shown in the x-ray projection image and (ii) the positions of the second part.

9. The system of claim 1, wherein the computer program is further run to:
 determining the positions of the second part by at least one of an optical technique and a magnetic technique.

10. The system of claim 1, further comprising:
 a display that displays a representation of the first part at the positions of the first part within the provided image data set.

11. The system of claim 1, further comprising:
 the interventional instrument.

12. A method for determining positions of an interventional instrument within a subject, the method comprising:
 providing an image data set of an interior of the subject as a provided image data set;
 subsequent to a first part of the interventional instrument being introduced into the subject, determining positions of a second part of the interventional instrument outside the subject;

generating an x-ray projection image, separate from the provided image data set, of the first part of the interventional instrument introduced within the subject;

determining a spatial relation between the positions of the second part and positions of the first part based on (i) the x-ray projection image of the first part introduced within the subject and (ii) the positions of the second part; and determining positions of the first part within the provided image data set, without having to further image the first part, based on images that are only from the provided image data set and the x-ray projection image, and based on the positions of the second part and the spatial relation between the positions of the second part and the positions of the first part, as determined via determining the spatial relation between the positions of the second part and the positions of the first part.

13. The method of claim 12,
wherein the method is implemented by a computer program of instructions embodied on a non-transitory computer program element and executable by a computer for determining positions of the interventional instrument within the subject, and in response to the computer program being executed on the computer.

14. The method of claim 12,
wherein the method is implemented by a computer program of instructions embodied on a non-transitory computer readable medium and executable by an interventional system for performing an interventional procedure, and in response to the computer program being executed on the computer.

15. A non-transitory computer readable medium containing a program, executable by a computer processor of a computer of a system for performing an interventional procedure on a subject,
wherein, when executed by the computer processor, the program causes the system for performing an interventional procedure to perform a process comprising:

providing an image data set of an interior of the subject as a provided image data set;

subsequent to a first part of an interventional instrument being introduced into the subject, determining positions of a second part of an interventional instrument outside the subject;

generating an x-ray projection image, separate from the provided image data set, of the first part of the interventional instrument introduced within the subject;

determining a spatial relation between the positions of the second part and positions of the first part based on (i) the x-ray projection image of the first part introduced within the subject and (ii) the positions of the second part; and determining positions of the first part within the provided image data set, without having to further image the first part, based on images that are only from the provided image data set and the x-ray projection image, and based on the positions of the second part, and the spatial relation between the positions of the second part and the positions of the first part, as determined in determining the spatial relation between the positions of the second part and the positions of the first part.

16. The method of claim 12,
wherein the image data set of the interior of the subject is generated before acquiring the x-ray projection image.

17. The method of claim 16,
wherein the image data set is generated by a computed tomography system.

18. The non-transitory computer readable medium of claim 15,
wherein the image data set of the interior of the subject is generated before acquiring the x-ray projection image.

19. The computer readable medium of claim 18,
wherein the image data set is generated by a computed tomography system.

* * * * *